US010013532B2

(12) United States Patent
Mizuhara

(10) Patent No.: US 10,013,532 B2
(45) Date of Patent: Jul. 3, 2018

(54) TERMINAL, SYSTEM, DISPLAY METHOD, AND RECORDING MEDIUM STORING A DISPLAY PROGRAM

(71) Applicant: Takuya Mizuhara, Kanagawa (JP)

(72) Inventor: Takuya Mizuhara, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 30 days.

(21) Appl. No.: 14/989,069

(22) Filed: Jan. 6, 2016

(65) Prior Publication Data

US 2016/0210432 A1 Jul. 21, 2016

(30) Foreign Application Priority Data

Jan. 20, 2015 (JP) ................................. 2015-008549

(51) Int. Cl.
*G06F 19/00* (2018.01)
*A61B 3/113* (2006.01)
*H04N 7/14* (2006.01)

(52) U.S. Cl.
CPC .......... *G06F 19/3418* (2013.01); *A61B 3/113* (2013.01); *H04N 7/147* (2013.01)

(58) Field of Classification Search
CPC ............................ G06F 19/3418; A61B 3/113
See application file for complete search history.

(56) References Cited

U.S. PATENT DOCUMENTS

| | | | |
|---|---|---|---|
| 6,003,991 A | * | 12/1999 | Viirre ...................... A61B 3/145 348/E13.014 |
| 7,460,150 B1 | | 12/2008 | Coughlan et al. |
| 2012/0092436 A1 | | 4/2012 | Pahud et al. |
| 2014/0168056 A1 | | 6/2014 | Swaminathan et al. |
| 2015/0365658 A1 | | 12/2015 | Devale |
| 2016/0018888 A1 | | 1/2016 | Buford |
| 2016/0127427 A1 | | 5/2016 | Bostick et al. |

FOREIGN PATENT DOCUMENTS

| | | |
|---|---|---|
| JP | 11-224152 | 8/1999 |
| JP | 2012-178135 | 9/2012 |

OTHER PUBLICATIONS

U.S. Appl. No. 15/989,536, filed Jan. 6, 2016.
Office Action for corresponding U.S. Appl. No. 14/989,536 dated May 1, 2018.

* cited by examiner

*Primary Examiner* — Donnell Long
(74) *Attorney, Agent, or Firm* — Harness, Dickey & Pierce, PLC

(57) ABSTRACT

A communication terminal for communicating with a counterpart communication terminal includes a receiver that receives image data including an eye image of a user operating the counterpart communication terminal from the counterpart communication terminal, the eye image of the user being captured at the counterpart communication terminal, and circuitry that specifies a sightline position indicating a sightline of the user based on the received image data including the eye image and controls a display to display sightline information indicating the sightline position of the user at the specified position.

12 Claims, 12 Drawing Sheets

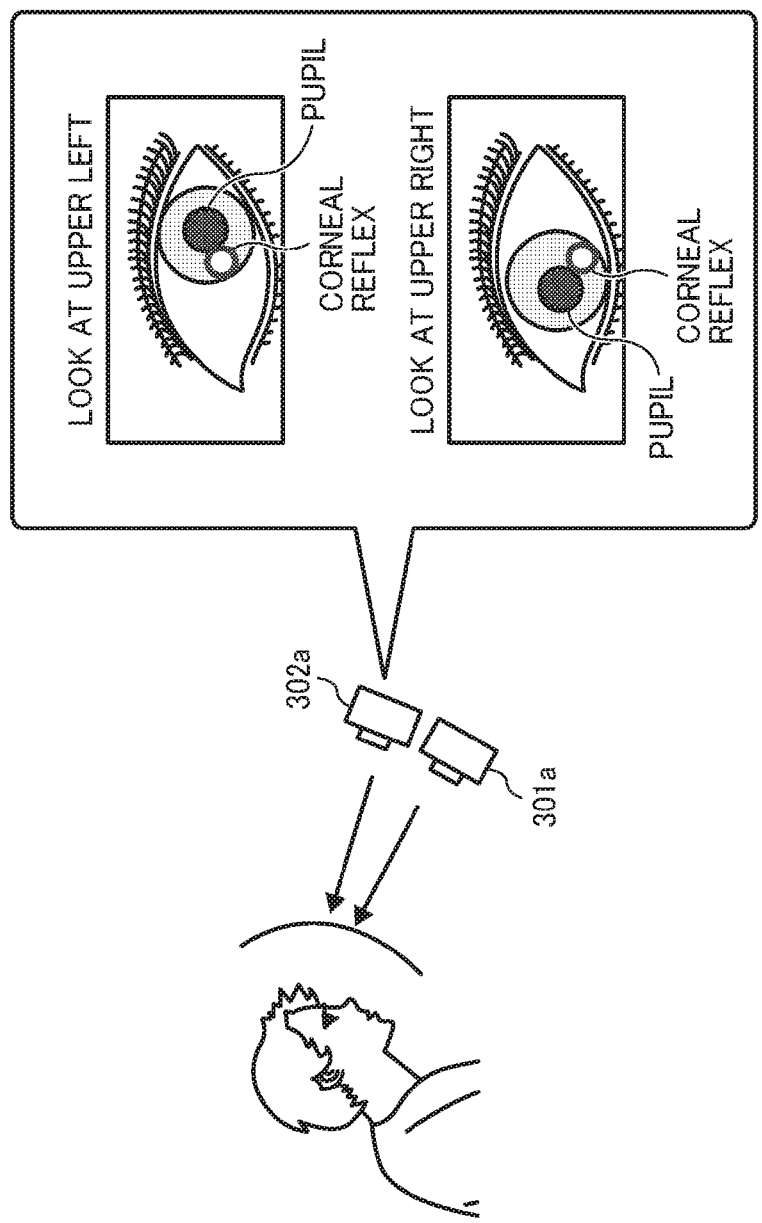

FIG. 3

MEDICAL CHECKUP DATA

| NAME | SEX | AGE |
|---|---|---|
| TARO RICOH | MALE | 36 |

| CHECKED ITEMS | 2014/05/01 | 2013/05/01 | 2012/05/01 | 2011/05/01 |
|---|---|---|---|---|
| HEIGHT | 170.5 | 170.4 | 170.6 | 170.8 |
| WEIGHT | 70.4 | 69.1 | 66.1 | 65.3 |
| BMI | 24.2 | 23.8 | 22.8 | 22.4 |
| BLOOD PRESSURE | 130 | 111 | 126 | 132 |
| URIC ACID | 6.4 | 6.5 | 6.8 | 6.1 |
| ERYTHROCYTE | 481 | 472 | 491 | 456 |
| NEUTRAL FAT | 172 | 178 | 173 | 167 |

| PAST MEDICAL HISTORY | ANSWERS |
|---|---|
| HIGH-BLOOD PRESSURE | YES |
| STROKE | NO |
| CANCER | NO |
| DIABETES | YES |
| ARRHYTHMIA | NO |
| BRONCHIAL ASTHMA | NO |

| LIFESTYLE HABITS | ANSWERS |
|---|---|
| EXERCISE HABIT | ONCE A WEEK |
| SMOKING | MORE THAN 10 PIECES A WEEK |
| DRINKING | 1 LITTER A WEEK |
| SLEEPING TIME | 6 HOURS (AVE) |
| EAT FRIED FOODS | YES |
| CONSTIPATION | NO |
| FEEL STRESSED | NO |

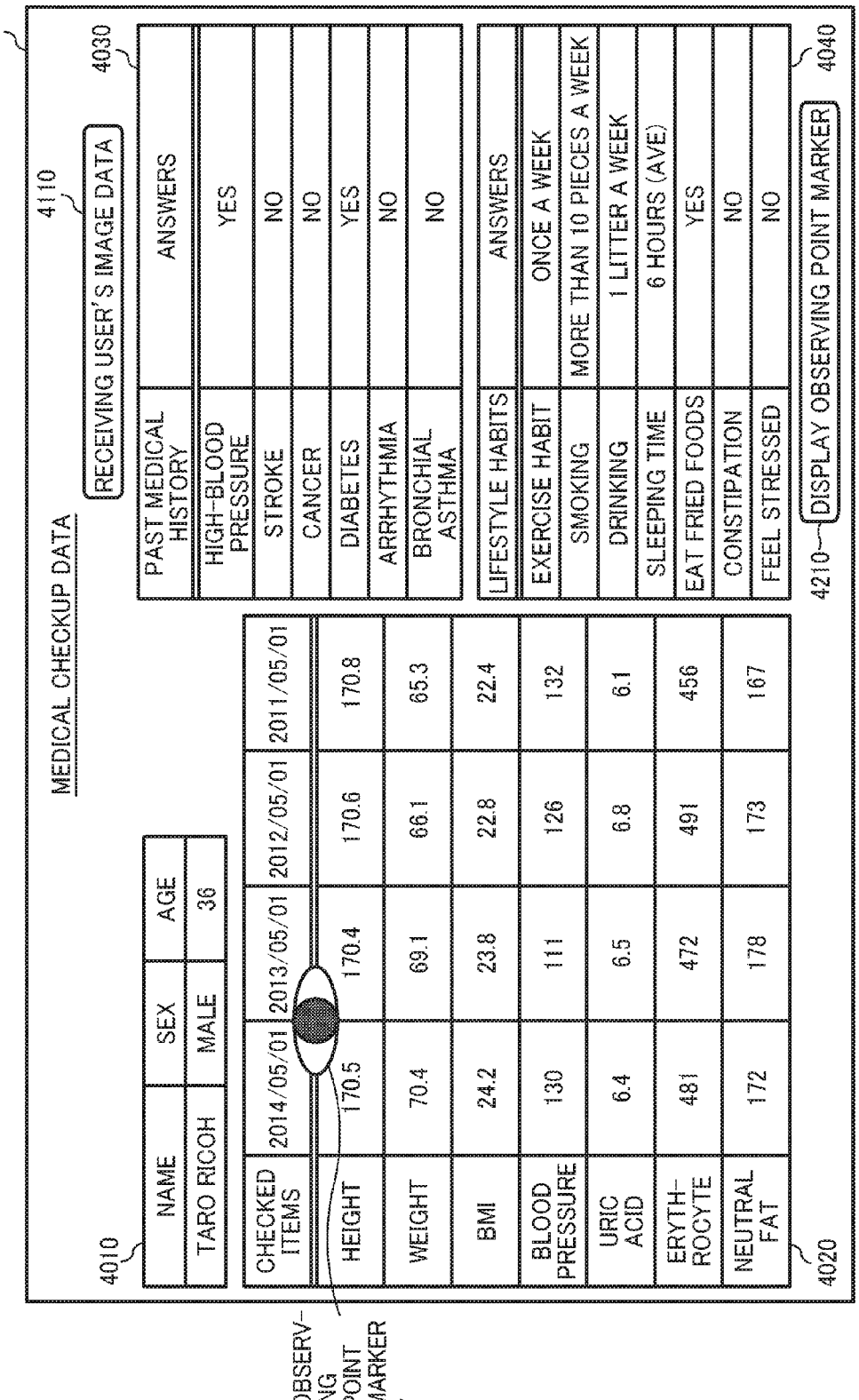

FIG. 7

| USER ID | NAME | SEX | AGE |
|---------|------|-----|-----|
| 123456 | TARO RICOH | MALE | 36 |
| 123457 | HANAKO PENTA | FEMALE | 35 |
| ⋮ | ⋮ | ⋮ | ⋮ |

FIG. 8A

| USER ID | CHECKED ITEMS | 2014/05/01 | 2013/05/01 | 2012/05/01 | 2011/05/01 |
|---|---|---|---|---|---|
| 12345 | HEIGHT | 170.5 | 170.4 | 170.6 | 170.8 |
| | WEIGHT | 70.0 | 69.1 | 66.1 | 65.3 |
| | BMI | 24.2 | 23.8 | 22.8 | 22.4 |
| | BLOOD PRESSURE | 130 | 111 | 126 | 132 |
| | URIC ACID | 6.4 | 6.5 | 6.8 | 6.1 |
| | ERYTH-ROCYTE | 481 | 472 | 491 | 456 |
| | NEUTRAL FAT | 172 | 178 | 173 | 167 |

FIG. 8B

| USER ID | PAST MEDICAL HISTORY | ANSWERS |
|---|---|---|
| 12345 | HIGH-BLOOD PRESSURE | YES |
| | STROKE | NO |
| | CANCER | NO |
| | DIABETES | YES |
| | ARRHYTHMIA | NO |
| | BRONCHIAL ASTHMA | NO |

FIG. 8C

| USER ID | LIFESTYLE HABITS | ANSWERS |
|---|---|---|
| 12345 | EXERCISE HABIT | ONCE A WEEK |
| | SMOKING | MORE THAN 10 PIECES A WEEK |
| | DRINKING | 1 LITTER A WEEK |
| | SLEEPING TIME | 6 HOURS (AVE) |
| | EAT FRIED FOODS | YES |
| | CONSTIPATION | NO |
| | FEEL STRESSED | NO |

| PUPIL-CORNEAL REFLEX | DISPLAY POSITIONS |
|---|---|
| (1, −1) | DISPLAY AREA s1 (UPPER LEFT) |
| (−1, −1) | DISPLAY AREA s2 (UPPER RIGHT) |
| (1, 1) | DISPLAY AREA s3 (LOWER LEFT) |
| (−1, 1) | DISPLAY AREA s4 (LOWER RIGHT) |

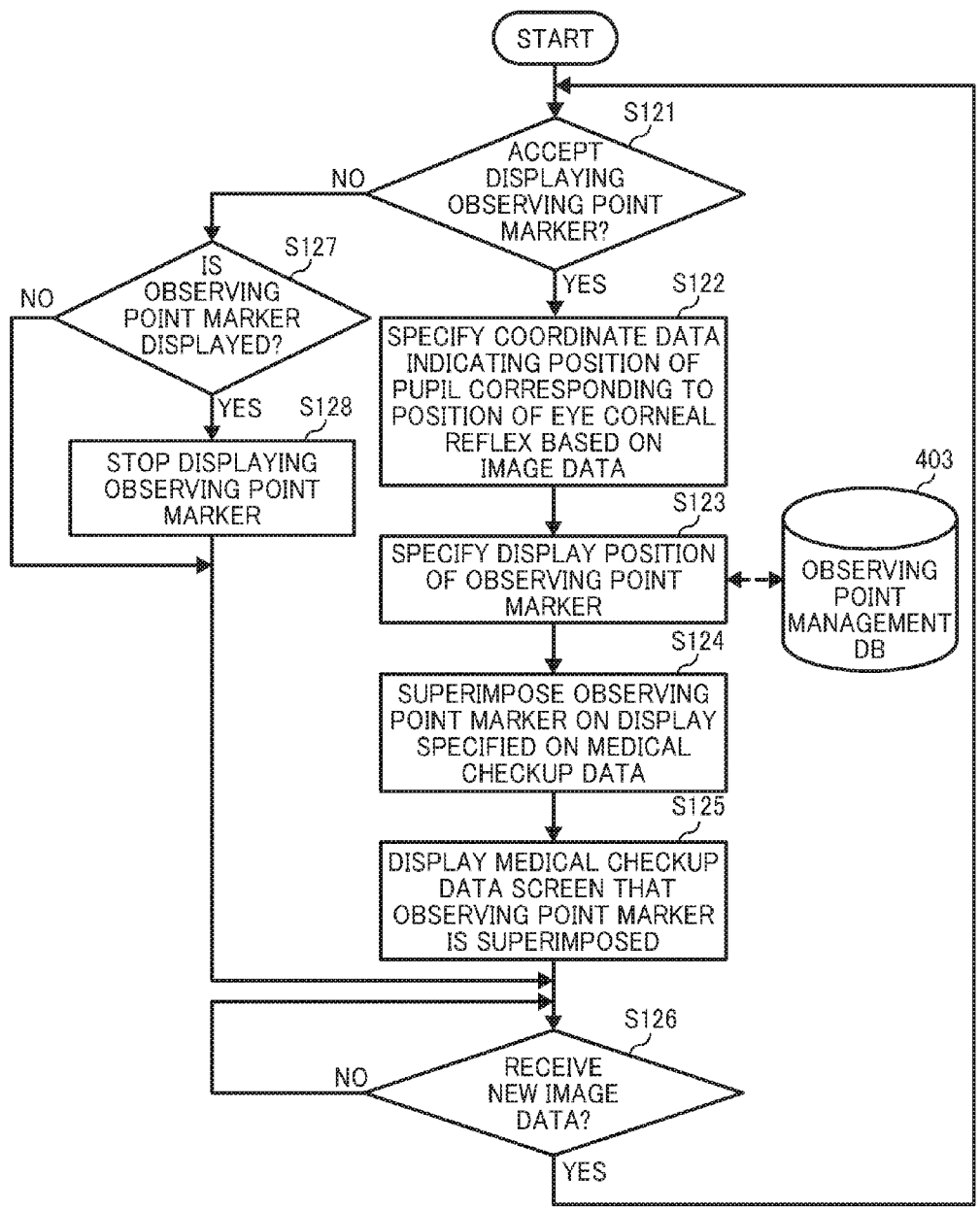

TERMINAL, SYSTEM, DISPLAY METHOD, AND RECORDING MEDIUM STORING A DISPLAY PROGRAM

CROSS-REFERENCE TO RELATED APPLICATIONS

This patent application is based on and claims priority pursuant to 35 U.S.C. § 119(a) to Japanese Patent Application No. 2015-008549, filed on Jan. 20, 2015 in the Japan Patent Office, the entire disclosures of which are hereby incorporated by reference herein.

BACKGROUND

Technical Field

The present invention relates to a terminal, a system, a display method, and a non-transitory recording medium storing a display program.

Background Art

Recently, videoconference systems for allowing a user to communicate with a counterpart at a remotely-located site via the Internet have been widely used. Since the videoconference systems allow the user to have conversation while watching a face of the counterpart, the user feels as he or she were having a face-to-face conversation with the counterpart locally.

It has become difficult to allocate industrial physicians to all offices from a viewpoint of labor cost. To cope with this issue, some industrial physicians use the videoconference systems to examine a patient at a remotely-located site.

SUMMARY

An example embodiment of the present invention provides a novel communication terminal for communicating with a counterpart communication terminal that includes a receiver that receives image data including an eye image of a user operating the counterpart communication terminal from the counterpart communication terminal, the eye image of the user being captured at the counterpart communication terminal, and circuitry that specifies a sightline position indicating a sightline of the user based on the received image data including the eye image and controls a display to display sightline information indicating the sightline position of the user at the specified position.

Further embodiments of the present invention provide a remote communication system, a display method, and a non-transitory recording medium storing a display program.

BRIEF DESCRIPTION I/F THE DRAWINGS

A more complete appreciation of the disclosure and many of the attendant advantages and features thereof can be readily obtained and understood from the following detailed description with reference to the accompanying drawings, wherein:

FIG. 2 is a schematic diagram illustrating a sightline detection method as an embodiment of the present invention;

FIG. 3 is a diagram illustrating an employee-side screen as an embodiment of the present invention;

FIG. 4 is a diagram illustrating an industrial-physician-side screen as an embodiment of the present invention;

FIG. 7 is a conceptual diagram illustrating a user management table as an embodiment of the present invention;

FIG. 8A is a diagram illustrating a checkup result management table;

FIG. 8B is a diagram illustrating a past medical history management table;

FIG. 8C is a diagram illustrating a lifestyle habits management table;

FIG. 12 is a flowchart illustrating operation of displaying an observing point marker on the industrial-physician-side screen, according to an embodiment of the present invention.

Figure 1:
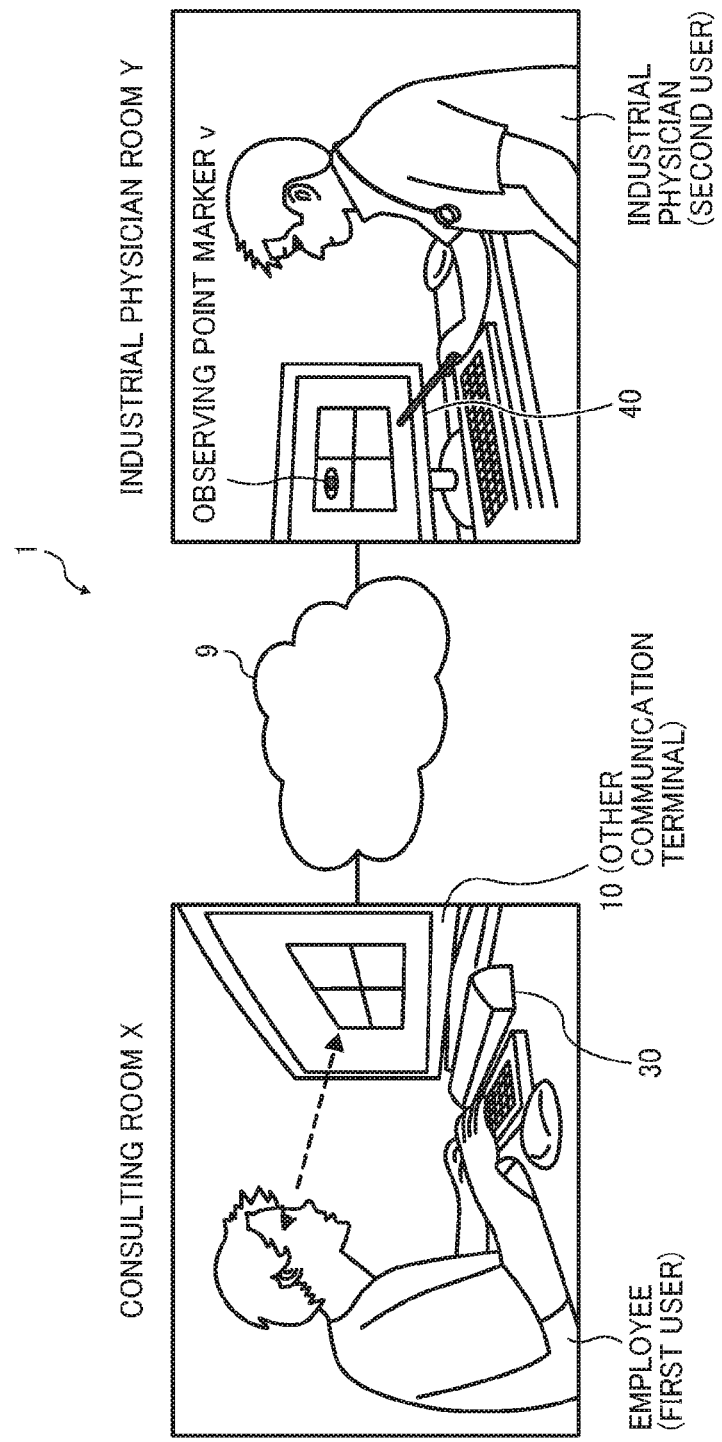
FIG. 1 is a schematic diagram illustrating a configuration of a consultation system as an embodiment of the present invention.

The accompanying drawings are intended to depict example embodiments of the present invention and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing preferred embodiments illustrated in the drawings, specific terminology is employed for the sake of clarity. However, the disclosure of this patent specification is not intended to be limited to the specific terminology so selected, and it is to be understood that each specific element includes all technical equivalents that have the same function, operate in a similar manner, and achieve a similar result.

Referring to FIGS. 1 to 4, an embodiment of the present invention is described. FIG. 1 is a schematic diagram illustrating a configuration of a consultation system 1 according to the embodiment.

As shown in FIG. 1, the consultation system 1 in this embodiment includes an employee-side communication terminal 10, an employee-side sightline detection device 30, and an industrial-physician-side communication terminal 40. The communication terminal 10 and the sightline detection device 30 are located at a consultation room X where an employee visits for consultation with an industrial physician. The sightline detection device 30 is connected to the communication terminal 10 via a cable for transferring image data including at least an image of an eye of the employee. The communication terminal 40 is located at an industrial physician's room Y where the industrial physician works.

In this embodiment, general-purpose personal computers (PCs) are used for the communication terminals 10 and 40, and they are connected with each other communicably via a communication network 9 such as the Internet and a local area network (LAN).

It should be noted that any one of the communication terminals 10 and 40 may be implemented by a smartphone or a tablet device. Furthermore, at least the communication terminal 10 may be a terminal with a build-in sightline detection device 30, such that the communication terminal 10 may be dedicated to the remote consultation. In this disclosure, the communication terminal 10 may be referred to as a first communication terminal, or a counterpart communication terminal from a viewpoint of the communication terminal 40. The communication terminal 40 may be referred to as a second communication terminal.

For example, in FIG. 1, the consultation system 1 is used by the employee as an example of the first user, and the industrial physician as an example of the second user. The other example combinations of the first user and the second user include a corporate manager as the first user and the industrial physician as the second user, or the employee or the corporate manager as the first user and any other physician, a nurse, or a pharmacist as the second user. The other example combinations of the first user and the second user further include a teacher or an instructor as the first user and a student of any age or a guardian of the student as the second user. Furthermore, the other example combinations of the first user and the second user include a subordinate as the first user and a boss as the second user.

In FIG. 1, the sightline detection device 30 transfers image data acquired by capturing at least the employee's eye part to the communication terminal 10, and the communication terminal 10 transfers the image data to the communication terminal 40. After receiving the image data, the communication terminal 40 displays an observing point marker v, which is added to reflect the sightline direction of the employee based on the image data. In this case, an eyeball-shaped marker is displayed as an example of the observing point marker v. In this case, an eyeball-shaped marker is displayed as an example of the observing point marker v. As a result, even in case of having a remote consultation with the employee, the industrial physician can perceive, from the unstable sightline, that the employee has some concerns or seems to be depressed, just like the face-to-face consultation.

It should be noted that the observing point marker v indicating the employee's sightline direction is not displayed on the communication terminal 10. This is because the industrial physician cannot determine whether or not the employee is in a depression etc. precisely if the employee recognizes his/her own observing point marker v. In addition, the observing point marker v is an example of observing point information. Other examples of the observing point information include not displaying the marker but modifying color of texts or width of frames etc. displayed as the medical checkup data.

Next, an outline of a sightline detection method is described below. FIG. 2 is a schematic diagram illustrating operation of detecting a sightline of the employee in this embodiment. The sightline detection method detects movements of the user's eyeballs to determine directions at which the user is looking. To start detecting movements of the user's eyeballs, firstly, a static part (reference point) and a movable part (moving point) of the user's eyes are detected at the detection device. After detecting the reference point and the moving point, the detection device detects the sightline of the user based on a position of the moving point in accordance with the reference point. There are various sightline detection methods, each of which differs in how the reference point and the moving point are each chosen. Among them, as a typical method, a sightline detection method in which corneal reflex is regarded as the reference point and the pupil is regarded as the moving point to analyze their positional relationship is described below.

In general, the detection device has an infrared light emitting diode (LED) lighting device 301a, which illuminates the user's face, and determines a position of reflected light of the emitted light on the cornea (the corneal reflex) as the reference point. The detection device further has an infrared camera 302a, which detects the user's sightline based on the position of the pupil with reference to the position of the corneal reflex. For example, as shown in FIG. 2, if the pupil of the left eye is located at upper left compared to the position of the corneal reflex, it is detected that the user is looking at upper left. By contrast, if the pupil of the left eye is located at upper right compared to the position of the corneal reflex, it is detected that the user is looking at upper right. The detection device may alternatively use visible ray instead of infrared ray.

In this embodiment, the sightline detection method described above is applied to detect the first user's sightline during remote consultation, which is performed by the terminal 10 at the employee side in cooperation with the terminal 40 at the industrial physician side. As a result, in this embodiment, a screen shown in FIG. 3 is displayed on the communication terminal 10 on the employee side, and a screen shown in FIG. 4 is displayed on the communication terminal 40 on the industrial physician side.

FIG. 3 is a diagram illustrating an employee-side screen in this embodiment. FIG. 4 is a diagram illustrating an industrial-physician-side screen in this embodiment. As shown in FIG. 3, the communication terminal 10 displays a medical checkup data screen 1000 on a display 217 (described later). On the medical checkup data screen 1000, a user's personal information display area 1010, a checkup result display area 1020, a medical history display area 1030, and a lifestyle habit display area 1040 are displayed. On the personal information display area 1010, the user's personal data such as employee name etc. is displayed. The medical checkup management data such as checkup results of the user's medical checkup etc. is displayed on the checkup result display area 1020, the medical history display area 1030, and the lifestyle habit display area 1040. That is, the user personal data and the medical checkup management data, which may be collectively referred to as the medical checkup data, is displayed as the content of the medical checkup data screen 1000. In this embodiment, the remote consultation is used for medical use. However, the purpose of the remote consultation is not limited to that. That is, it is possible to use the remote consultation for business use. As a result, the medical checkup data in this embodiment is an example of the user related data that indicates content related to the user. Other examples of the user related data are a performance result in an example case of a manager as the second user and a staff as the first user, a grade report or an examination sheet in an example case of a teacher as the second user and a student as the first user, an evidential photo or a questioning sheet in an example case of a detective as the second user and a suspect as the first user, and a fortune-telling result or an image of a palm in an example case of a fortune-teller as the second user and a customer as the first user.

By contrast, the communication terminal 40 displays a medical checkup data screen 4000 on a display 217 (described later). On the medical checkup data screen 4000, just like the screen of FIG. 3, a user's personal information display area 4010, a checkup result display area 4020, a medical history display area 4030, and a lifestyle habit display area 4040 are displayed. The user's personal information display area 4010, the checkup result display area 4020, the medical history display area 4030, and the lifestyle habit display area 4040 respectively display the same content as the corresponding user's personal information display area 1010, checkup result display area 1020, medical history display area 1030, and lifestyle habit display area 1040. The medical checkup data screen 4000 additionally displays an observing point marker v, a reception status display area 4110, and an observing point marker display button 4210. On the reception status display area 4110, a message indicating that the communication terminal 40 is receiving image data from the communication counterpart (i.e., the employee) is displayed. In this case, the message "receiving user's image data" is displayed as an example of the message. The observing point marker display button 4210 is a key pressed by the industrial physician to display the observing point marker v on the display 217 at the communication terminal 40. That is, the observing point marker display button 4210 accepts a command to display the observing point marker v from the industrial physician. It should be noted that the displayed position of the observing point marker v on the medical checkup data screen 4000 changes to reflect the employee's sightline direction that is currently detected.

Figure 5:
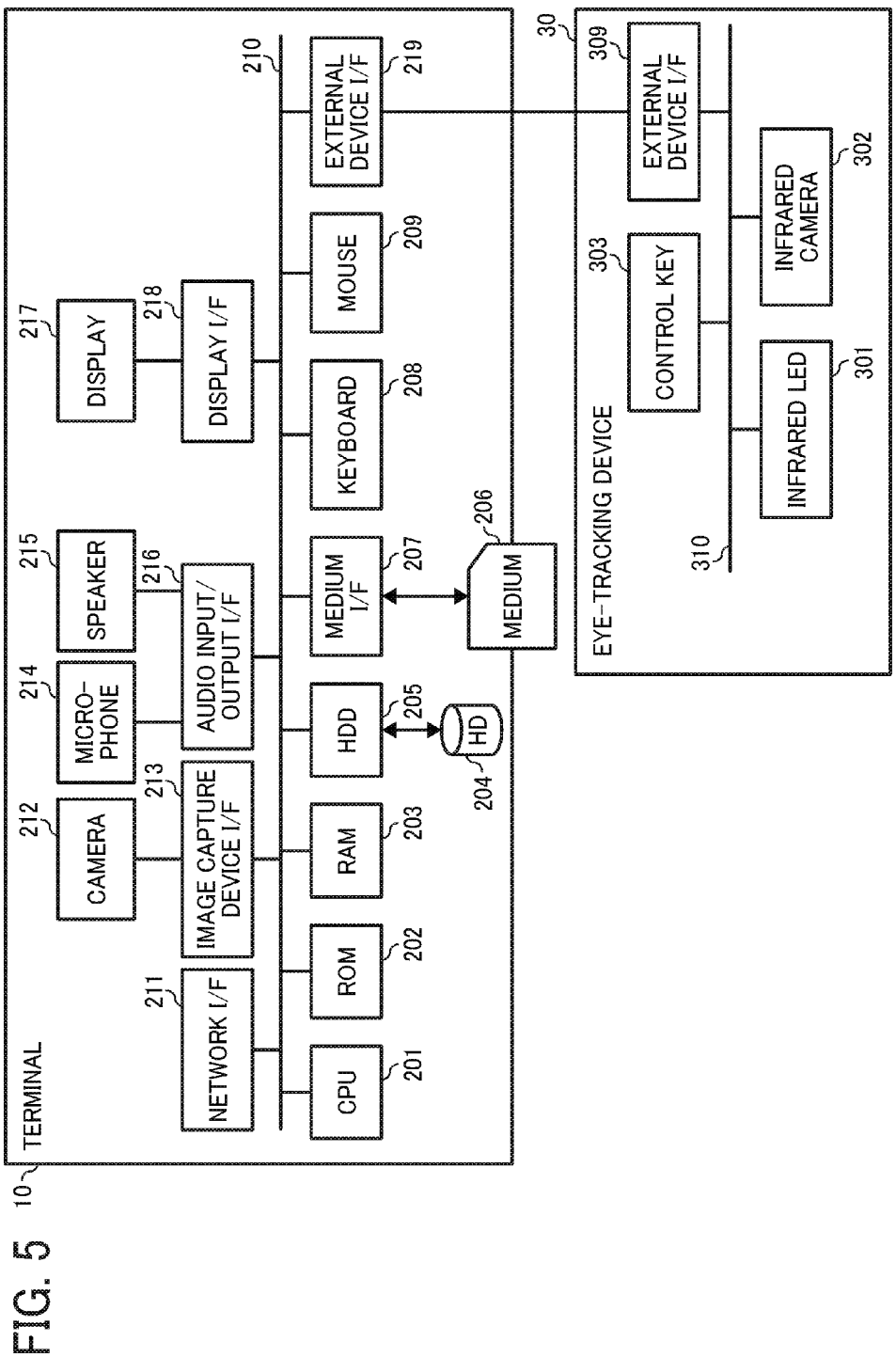
FIG. 5 is a diagram illustrating a hardware configuration of a communication terminal and a sightline detection device of the consultation system of FIG. 1 as the embodiment of the present invention.

Next, a hardware configuration of the communication terminals 10 and 40 and the sightline detection device 30 is described below with reference to FIG. 5. FIG. 5 is a diagram illustrating a hardware configuration of the communication terminal 10 and the sightline detection device 30 in this embodiment. Here, the communication terminal 40 has the same configuration as that of the communication terminal 10. Therefore, description of the communication terminal 40 is omitted, and the hardware configuration of the communication terminal 10 and the sightline detection device 30 is described below.

As shown in FIG. 5, the communication terminal 10 includes a central processing unit (CPU) 201, a read only memory (ROM) 202, a random access memory (RAM) 203, a hard disk (HD) 204, a hard disk drive (HDD) 205, a medium interface (I/F) 207, a keyboard 208, and a mouse 209.

Among those components, the CPU 201 controls entire operation of the communication terminal 10. The ROM 202 stores programs such as IPL etc. used for executing the CPU 201. The RAM 203 is used as a work area for the CPU 201. The HD 204 stores various data such as programs. The HDD 205 controls reading various data from the HD 204 and writing various data in the HD 204 under control of the CPU 201. The medium I/F 207 controls reading data from a recording medium such as a flash memory etc. and writing data in the recording medium 206. The keyboard 208 is an input device including multiple keys for inputting text, values, and various commands. The mouse 209 is an input device used for selecting or executing various commands, selecting a target to be processed, and moving a cursor etc.

In addition, the communication terminal 10 includes a network I/F 211, a camera 212, an image capture device I/F 213, a microphone 214, a speaker 215, an audio input/output I/F 216, a display 217, a display I/F 218, and an external device I/F 219.

Among those components, the network I/F 211 is an interface for transferring data via the communication network 9, such as a network interface card. The camera 212 captures a target object under control of the CPU 201 and outputs image data of the captured image. The image capture device I/F 213 is a circuit for controlling driving the camera 212. The microphone 214 is a built-in microphone for inputting audio such as audio of user's voice. The speaker 215 is a built-in speaker for outputting audio such as audio of the counterpart user's voice. The audio input/output I/F 216 is a circuit for processing input of an audio signal from the microphone 214 and output an audio signal to the speaker 215 under control of the CPU 201. The display 217 displays various information such as a cursor, a menu, a window, a text, a marker, and an image etc. The display I/F 218 outputs video (a still image and/or a movie) to the display 217 under control of the CPU 201. The external device I/F 219 is an interface for transferring data via a Universal Serial Bus (USB) cable etc.

Furthermore, the communication terminal 10 includes a bus line 210 such as an address bus and a data bus etc. for electrically connecting the components such as the CPU 201 described above with each other as shown in FIG. 5.

The programs described above may be stored as installable or executable files in a computer-readable recording medium such as the recording medium 206 described above for distribution. Alternatively, the programs described above may be stored not in the HD 204 but in the ROM 202. Other examples of the above-described recording medium include, but not limited to, a Compact Disc Recordable (CD-R), a Digital Versatile Disc (DVD), and a Blu-ray disc.

As shown in FIG. 5, the sightline detection device 30 includes an infrared LED lighting device 301, an infrared camera 302, a control key 303, an external device I/F 309, and a bus line 310.

Among those components, the infrared LED lighting device 301 is a lighting device including a diode that emits infrared light. The infrared camera 302 senses infrared. The external device I/F 309 is an interface for transferring data via a USB cable etc. The bus line 310 is a bus such as an address bus and a data bus etc. for electrically connecting the components such as the infrared LED lighting device 301 etc. described above with each other as shown in FIG. 5.

Figure 6:
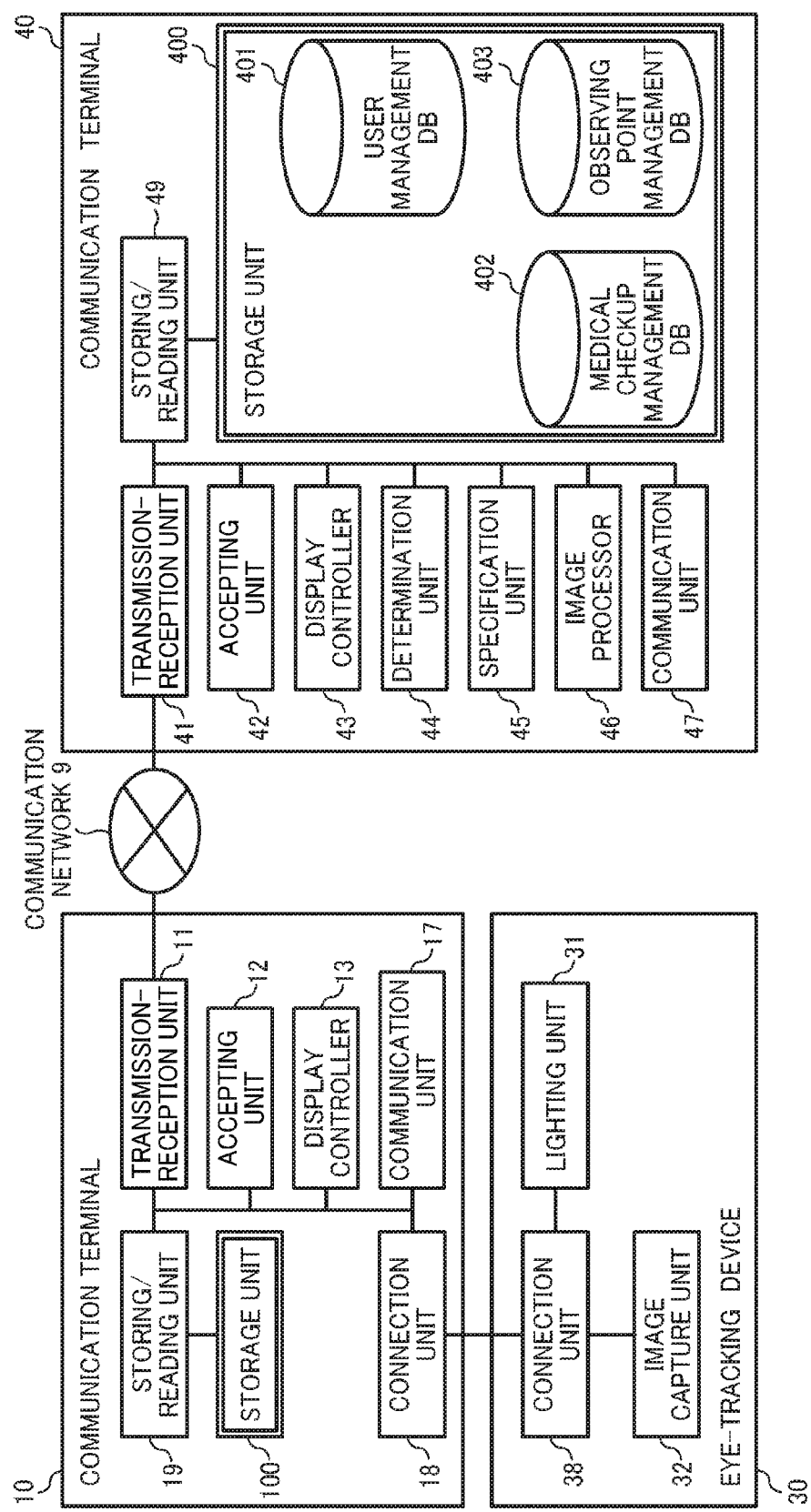
FIG. 6 is a diagram illustrating a functional configuration of the consultation system of FIG. 1.

Next, a functional configuration of the consultation system 1 in this embodiment is described below with reference to FIGS. 5 and 6. FIG. 6 is a diagram illustrating a functional configuration of the consultation system 1 in this embodiment.

As shown in FIG. 6, the communication terminal 10 includes a transmission-reception unit 11, an accepting unit 12, a display controller 13, a communication unit 17, a connection unit 18, and a storing/reading unit 19. Those components described above are functions or units implemented by operating some of the hardware components shown in FIG. 5 under control of the CPU 201 in accordance with programs expanded in the RAM 203 from the HD 204. In addition, the communication terminal 10 includes a storage unit 100 that may be implemented by the ROM 202, the RAM 203, and/or the HD 204 shown in FIG. 5.

The transmission-reception unit 11 in the communication terminal 10 is mainly implemented by processes performed by the network I/F 210 and the CPU 201 shown in FIG. 5.

Mainly, the transmission-reception unit 11 transfers various data to the communication terminal 40 or receives various data from the communication terminal 40 via the communication network 9. For example, every time the infrared camera 302 captures an image of the employee at a predetermined interval, the transmission-reception unit 11 transmits image data including an image of the employee's eye.

The accepting unit 12 is mainly implemented by processes performed by the keyboard 208, the mouse 209, and the CPU 201 and accepts various selection, designation, or commands etc. by user operation.

The display controller 13 is mainly implemented by processes performed by the display I/F 218 and the CPU 201 and controls displaying various images and text on the display 217.

The communication unit 17 is mainly implemented by processes performed by the camera 212, the image capture device I/F 213, the microphone 214, the speaker 215, the audio input/output I/F 216, the display 217, the display I/F 218, and the CPU 201 and communicates audio and video to the counterpart communication terminal 40 to carry out communication between the communication terminals 10 and 40.

The connection unit 18, which is mainly implemented by processes performed by the external device I/F 209 and the CPU 201, detects a connection to an external device, and communicates with the external device that is connected.

The storing/reading unit 19 stores various data in the storage unit 100 and reads various data from the storage unit 100.

As shown in FIG. 6, the sightline detection device 30 includes a lighting unit 31, an image capture unit 32, and a connection unit 38. Those components described above are functions or units implemented by operating some of the hardware components in the sightline detection unit 30 shown in FIG. 5.

The lighting unit 31 is implemented by operations of the infrared LED lighting device 301 and illuminates the user face by emitting infrared light.

The image capture unit 32 is implemented by operations of the infrared camera 302 as an example of the image capture unit and captures reflected light of the infrared emitted by the lighting unit 31 to generate image data.

The connection unit 38, which is mainly implemented by processes performed by the external device I/F 309, detects a connection to an external device and communicates with the external device that is connected.

As shown in FIG. 6, the communication terminal 40 includes a transmission-reception unit 41, an accepting unit 42, a display controller 43, a determination unit (determining unit) 44, a specification unit 45, an image processor 46, a communication unit 47, and a storing/reading unit 49. Those components described above are functions or units implemented by operating some of the hardware components shown in FIG. 5 under control of the CPU 201 in accordance with programs expanded in the RAM 203 from the HD 204. In addition, the communication terminal 40 includes a storage unit 400 that may be implemented by the ROM 202, the RAM 203, and/or the HD 204 shown in FIG. 5. The storage unit 400 stores therein a user management database (DB) 401 that consists of a user management table. The storage unit 400 further stores a medical checkup management DB 402 that consists of a checkup result management table, a medical history management table, and a lifestyle habit management table. Furthermore, the storage unit 400 stores an observing point position management DB 403 that consists of an observing point position management table.

It should be noted that the user management table stores various data to be used as the contents of user personal data. The checkup result management table, the medical history management table, and the lifestyle habit management table together store various data to be used as the contents of the medical checkup management data. That is, in FIGS. 3 and 4, the user management table has contents to be displayed in the user personal information display area 1010 (4010), the checkup result management table has contents to be displayed in the checkup result display area 1020 (4020), the medical history management table has contents to be displayed in the medical history display area 1030 (4030), and the lifestyle habit management table has contents to be displayed in the lifestyle habit display area 1040 (4040).

FIG. 7 is a conceptual diagram illustrating a user management table in this embodiment. The user management table, which is used to manage user personal information, stores, for each user, a user ID for identifying the user, a user name, a user sex, and a user age associated with each other. It should be noted that the user ID is an example of user identification information for uniquely identifying a user. Examples of the user identification information include an employee number, a student number, and a social security number, which may be managed using the computerized personal data system.

FIG. 8A is a conceptual diagram illustrating the checkup result management table. The checkup result management table stores a plurality of checkup items and past checkup dates for each check item in association with the user ID. Examples of the checked items include height, weight, Body Mass Index (BMI), blood pressure, uric acid, erythrocyte, and neutral fat.

FIG. 8B is a conceptual diagram illustrating the medical history management table. The medical history checkup table stores a plurality of past medical history items and user answers to questions regarding the past medical history items, in association with the user ID. Examples of the past medical history items include high-blood pressure, stroke, cancer, diabetes, arrhythmia, and bronchial asthma. If the answer is "yes", that indicates that the user has been diagnosed as having that disease, and if the answer is "no", that indicates that the user has not been diagnosed as having that disease.

FIG. 8C is a conceptual diagram illustrating the lifestyle habits management table. The lifestyle habit management table stores a plurality of lifestyle habit items and user's answers to questions of lifestyle habits in association with the user ID. Examples of the lifestyle habit items include exercise habit, smoking, drinking, sleeping time, eating many fried foods, constipation, and feeling stressed. If the answer is "yes", that indicates that the user practices the lifestyle habit item, and if the answer is "no", that indicates that the user does not practice the lifestyle habit item.

Figures 9A, 9B:
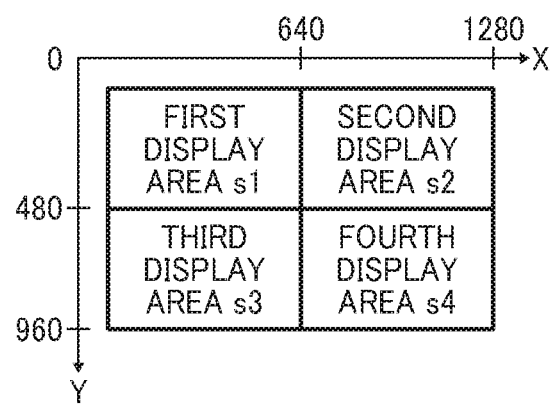
FIG. 9A is a diagram illustrating a sightline position management table.
FIG. 9B is a diagram for explaining a display position.

FIG. 9A is a conceptual diagram illustrating a sightline position management table. The sightline position management table stores coordinate data indicating a position of the pupil against a position of the corneal reflex of a user eye, in association with display position information indicating a position of the user observing point on the display 217 at the communication terminals 10 and 40.

FIG. 9B is a conceptual diagram illustrating a display position. In FIG. 9B, the respective displays 217 in the communication terminals 10 and 40 have a size of 1280 pixels horizontally by 960 pixels vertically. The upper left area corresponds to a first display area s1, the upper right area corresponds to a second display area s2, the lower left area corresponds to a third display area s3, and the lower right area corresponds to a fourth display area s4. For example, if the coordinate data of the user's pupil is (1, −1), the observing point position is located at the first display area s1. As a result, the observing point marker v is displayed in the middle of the first display area s1 as shown in FIG. 4.

Next, the functional configuration of the communication terminal 40 is described below with reference to FIGS. 5 and 6, according to the embodiment of the present invention.

The transmission-reception unit 41 in the communication terminal 40 is mainly implemented by processes performed by the network I/F 210 and the CPU 201 shown in FIG. 5. Mainly, the transmission-reception unit 41 transfers various data to the communication terminal 10 or receives various data from the communication terminal 10 via the communication network 9.

The accepting unit 42 is mainly implemented by processes performed by the keyboard 208, the mouse 209, and the CPU 201 and accepts various selection, designation, or commands etc. by user operation.

The display controller 43 is mainly implemented by processes performed by the display I/F 218 and the CPU 201 and controls displaying various images and text on the display 217.

The determination unit 44 is mainly implemented by processes performed by the CPU 201 and determines whether or not the image data is received from the communication terminal 10.

The specification unit 45 is mainly implemented by processes performed by the CPU 201 and specifies the employee's observing point position on the display 217 of the communication terminal 40 based on the image data received by the transmission-reception unit 41 every time the transmission-reception unit 41 receives the image data.

The image processor 46 is mainly implemented by processes performed by the CPU 201 and superimposes the observing point marker v on the medical checkup data.

The communication unit 47 is mainly implemented by processes performed by the camera 212, the image capture device I/F 213, the microphone 214, the speaker 215, the audio input/output I/F 216, the display 217, the display I/F 218, and the CPU 201 and communicates audio and video to the counterpart communication terminal 10 to carry out communication between the communication terminals 10 and 40.

The storing/reading unit 49 stores various data in the storage unit 400 or reads various data from the storage unit 400.

Figure 10:
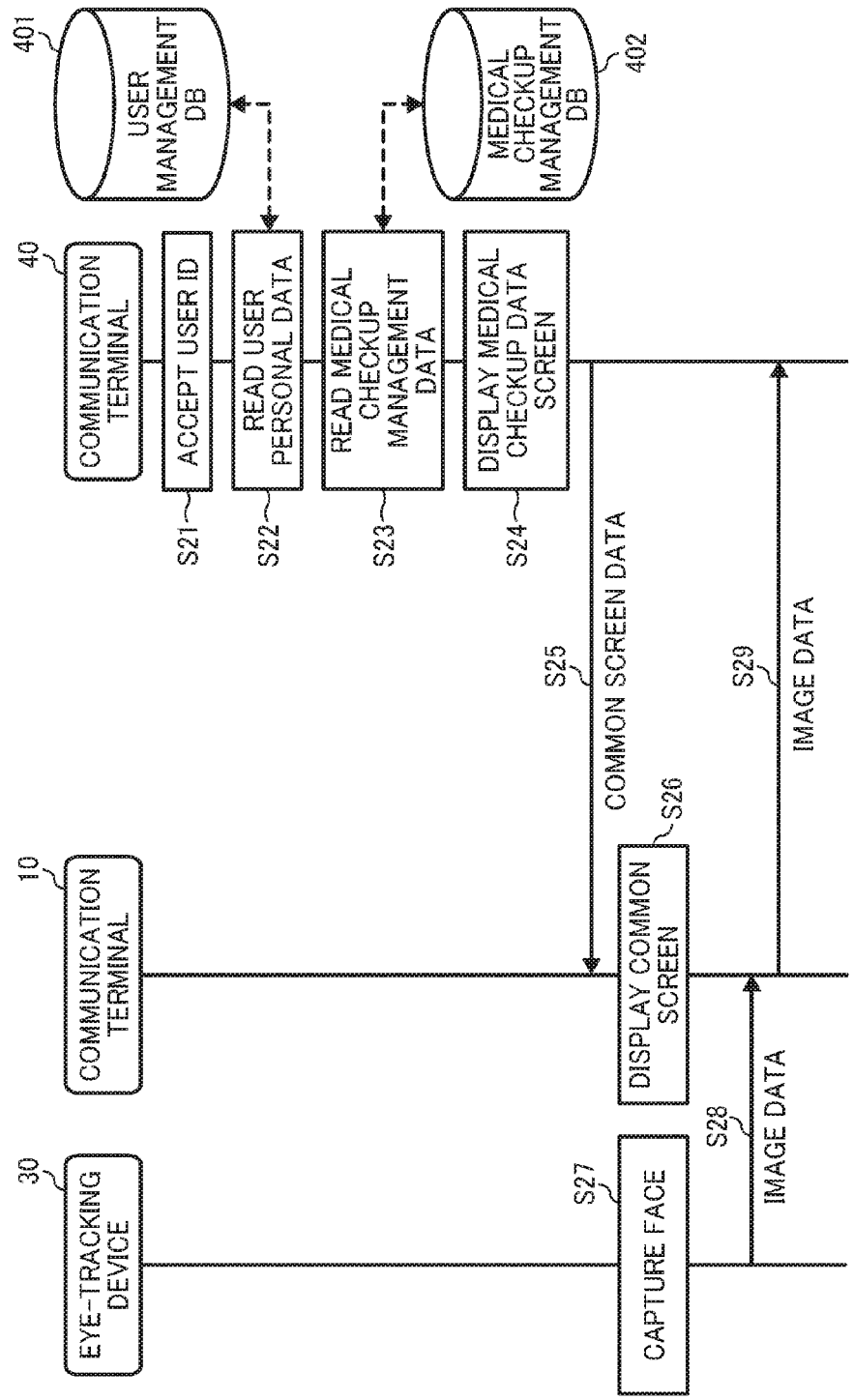
FIG. 10 is a sequence diagram illustrating operation of conducting a remote consultation, according to an embodiment of the present invention.
Figure 11:
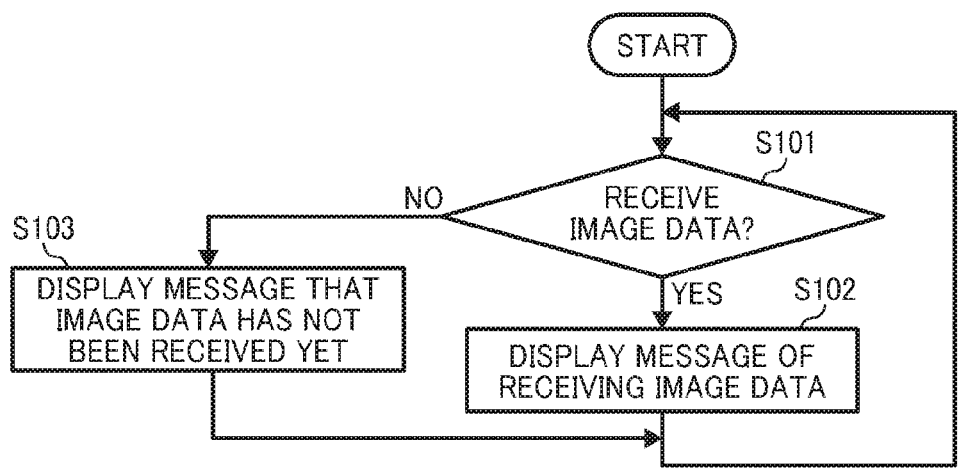
FIG. 11 is a flowchart illustrating operation of displaying a message on the industrial-physician-side screen, according to an embodiment of the present invention.

Next, processes and operations in this embodiment are described below with reference to FIGS. 10 to 12. FIG. 10 is a sequence diagram illustrating operation of carrying out a remote consultation. FIG. 11 is a flowchart illustrating operation of displaying a message on the industrial-physician-side screen. FIG. 12 is a flowchart illustrating operation of displaying the observing point marker on the industrial-physician-side screen.

First, just like the videoconference session, the employee and the industrial physician start the remote consultation using the communication terminals 10 and 40. At this point, the face of the user and at least a part of the room where the user resides at a counterpart site are displayed on the display 217 at a site where the user communicating with the counterpart user resides. As the industrial physician switches the current screen into an input screen and inputs the employee's user ID during the consultation, the accepting unit 42 receives input of the user ID in S21. Next, using the user ID accepted by the accepting unit 42 as a retrieval key, the storing/reading unit 49 searches through the user management table in the storage unit 400 (shown in FIG. 7) to read the user personal data indicating the corresponding user name, user sex, and user age for the user with the input user ID in S22. Furthermore, using the user ID accepted by the accepting unit 42 as the retrieval key, the storing/reading unit 49 searches through the medical checkup management table in the storage unit 400 (shown in FIG. 8) to read the medical checkup management data related to the corresponding user checkup items, user past medical history, and user lifestyle habits in S23. Subsequently, in the communication terminal 40, the display controller 43 displays the medical checkup data screen that consists of the user personal data and the medical checkup management data shown in FIG. 4 on the display 217 in the communication terminal 40 in S24. At this point, the observing point marker v and the message in the reception status display area 4110 have not been displayed yet.

Next, the transmission-reception unit 41 transfers shared screen data the same images as the display areas 4010, 4020, 4030, and 4040 to share the screen with the communication terminal 10 in S25. As a result, the transmission-reception unit 11 in the communication terminal 10 receives the shared screen data. Subsequently, in the communication terminal 10, the display controller 13 displays the medical checkup data screen shown in FIG. 3 on the display 217 in the communication terminal 10 in S26.

In addition, in the consultation room X, the lighting unit 31 in the sightline detection device 30 emits infrared light to the employee face, and the image capture unit 32 receives the reflected light to acquire the image data regarding the image including the employee eye in S27. The emission and reception operation are performed at a predetermined interval (e.g., every 0.5 seconds). Subsequently, the sightline detection device 30 transfers the image data from the connection unit 38 to the connection unit 18 in the communication terminal 10 in S28.

Next, the transmission-reception unit 11 in the communication terminal 10 transfers the image data to the communication terminal 40 via the communication network 9 in S29. As a result, the transmission-reception unit 41 in the communication terminal 40 receives the image data. The transmission/reception process of the image data described above is performed sequentially every time the sightline detection device 30 transfers the image data to the communication terminal 10 in S28.

Next, as shown in FIG. 11, in the communication terminal 40, the determination unit 44 determines whether or not the image data is received from the communication terminal 10 in S101. If the determination unit 44 determines that the image data is received (YES in S101), as shown in FIG. 4, the display controller 43 displays a receiving message indicating that the image data is being received in the reception status display area 4110 on the medical checkup data screen 4000 in S102. For example, as shown in FIG. 4, a message "receiving user's image data" is displayed as the receiving message. By contrast, if the determination unit 44 determines that the image data is not received from the communication terminal 10 (NO in S101), the display controller 43 displays a not-received message indicating that the image data has not been received yet in the reception status display area 4110 on the medical checkup data screen 4000 in S103. For example, a message "user's image data has not been received yet" is displayed as the not-received message. It should be noted that it is possible not to display a message if the image data has not been received.

Furthermore, as shown in FIG. 12, in the communication terminal 40, the determination unit 44 determines whether or not the accepting unit 42 accepts that the industrial physician requests to display the observing point marker v in S121. If the determination unit 44 determines that the request has been received (YES in S121), the specification unit 45 specifies coordinate data indicating a position of pupil against a position of corneal reflex of the eye based on the image data in S122. In addition, by searching through the sightline position management table in FIG. 9A using the coordinate data specified in S122 as the retrieval key, the specification unit 45 specifies a display position of the observing point marker v by reading corresponding display position information in S123.

Next, the image processor 46 superimposes the observing point marker v at the display position specified in S123 described above on the medical checkup data in S124. Subsequently, in the communication terminal 40, as shown in FIG. 4, the display controller 43 displays the medical checkup data screen 4000 on which the observing point marker v is imposed on the display 217 in the communication terminal 40 in S125.

After that, the determination unit 44 determines whether or not new image data is received in S126. Subsequently, in S126, if the determination unit 44 determines that the new image data is received (YES in S126), the process goes back to the step in S121. By contrast, in S126, if the determination unit 44 determines that the new image data has not been received yet (NO in S126), the determination unit 44 repeats the step in S126. For example, the repetition process is performed every one second.

By contrast, in S121, if the determination unit 44 determines that the request to display the observing point marker v has not been received yet (NO in S121), the determination unit 44 further determines whether or not the display controller 43 has already been displaying the observing point marker v in S127. If the determination unit 44 determines that the display controller 43 has already been displaying the observing point marker v (YES in S127), the display controller 43 stops displaying the observing point marker v in FIG. 4 in S128, and the process proceeds to S126. If the determination unit 44 determines that the display controller 43 is not displaying the observing point marker v (NO in S127), the process proceeds to S126. As shown in FIG. 4, if the observing point marker v is kept displaying on the medical checkup data screen 4000, the industrial physician might feel that it is difficult to recognize the medical checkup data screen 4000 in some cases. Therefore, it is possible to switch the observing point marker v from being displayed to not being displayed.

As described above, by displaying the observing point marker v on the display 217 in the communication terminal 40 on the industrial physician's side, the industrial physician can carry out the remote consultation considering the employee's sightline just like the face-to-face consultation. By using the communication terminal in this embodiment described above, it is possible to carry out the remote interview with quality similar to the face-to-face interview.

For example, as shown in FIG. 4, in case of displaying the observing point marker v at a position different from the employee's name even if the industrial physician confirms the employee's name through the communication the industrial physician can recognize that the employee is in some kind of abnormal condition such as depression.

Especially, if positions where the observing point marker v vary frequently under the control of the display controller 43 based on the image data transferred from the communication terminal 10 sequentially, the industrial physician can further recognize that the employee is in abnormal condition more easily since the employee's sightline is unstable.

Numerous additional modifications and variations are possible in light of the above teachings. It is therefore to be understood that, within the scope of the appended claims, the disclosure of this patent specification may be practiced otherwise than as specifically described herein.

For example, while the above-described embodiment describes the case where an image of both eyes of the user is used to detect the user's sightline, at least one eye of the user may be captured as long as the user's sightline can be detected. For instance, if the user's dominant eye can be specified, the user's sightline may be detected using the image of the user's dominant eye.

As can be appreciated by those skilled in the computer arts, this invention may be implemented as convenient using a conventional general-purpose digital computer programmed according to the teachings of the present specification. Appropriate software coding can readily be prepared by skilled programmers based on the teachings of the present disclosure, as will be apparent to those skilled in the software arts. The present invention may also be implemented by the preparation of application-specific integrated circuits or by interconnecting an appropriate network of conventional component circuits, as will be readily apparent to those skilled in the relevant art.

Each of the functions of the described embodiments may be implemented by one or more processing circuits. A processing circuit includes a programmed processor. A processing circuit also includes devices such as an application specific integrated circuit (ASIC) and conventional circuit components arranged to perform the recited functions.

What is claimed is:

1. A communication terminal for communicating with a counterpart communication terminal, the communication terminal comprising:
   a receiver configured to receive image data from the counterpart communication terminal, the received image data including an eye image of an eye of a user operating the counterpart communication terminal, the eye image of the user being captured at the counterpart communication terminal; and
   circuitry configured to
      specify a sightline position indicating a sightline of the user based on the received image data including the eye image, and
      control a display to display sightline information indicating the sightline position of the user at the specified sightline position.

2. The communication terminal according to claim 1, wherein the circuitry is configured to specify the sightline position of the user in response to the receiver receiving the image data including the eye image.

3. The communication terminal according to claim 1, further comprising:
   a user interface configured to receive a request associated with displaying the sightline information or not displaying the sightline information,
   wherein the circuitry is configured to selectively displays the sightline information on the display based on a determination of whether the request received at the user interface is the request associated with displaying the sightline information or the request associated with not displaying the sightline information.

4. The communication terminal according to claim 1, wherein the circuitry is configured to display the sightline information and user related data indicating information associated with the user on the display.

5. The communication terminal according to claim 4, wherein the circuitry is configured to
   superimposes the sightline information on the user related data, and
   displays the superimposed sightline information and the user related data on the display.

6. The communication terminal according to claim 5, further comprising a memory configured to store the user related data.

7. The communication terminal according to claim 4, further comprising:
   a transmitter configured to transmit shared screen data to the counterpart communication terminal to share a screen of the user related data that does not include the sightline information with the counterpart communication terminal.

8. The communication terminal according to claim 1, wherein the circuitry is configured to specify the sightline position of the user based on a position of a pupil of the eye of the user against a position of a corneal reflex of the eye of the user in the image data.

9. The communication terminal according to claim 8, wherein the circuitry is configured to
   manage a plurality of combinations of coordinate data indicating the position of the pupil of the eye of the user against the position of the corneal reflex of the eye of the user and display position information indicating the sightline position of the user on the display and
   specify the sightline position of the user on the display based on the display position information associated with the coordinate data indicating the position of the pupil of the eye of the user against the position of the corneal reflex of the eye of the user.

10. The communication terminal according to claim 1, wherein the sightline information is an eyeball-shaped marker.

11. A system, comprising at least one of the communication terminal and the counterpart communication terminal according to claim 1.

12. The system according to claim 11, wherein the counterpart communication terminal is configured to transmit the image data including the eye image of the user in response to a camera of the counterpart communication terminal capturing one or more images of the user at a particular interval.

* * * * *